US006823044B2

(12) United States Patent
Rosner

(10) Patent No.: US 6,823,044 B2
(45) Date of Patent: Nov. 23, 2004

(54) SYSTEM FOR COLLECTING MULTIPLE X-RAY IMAGE EXPOSURES OF A SAMPLE USING A SPARSE CONFIGURATION

(75) Inventor: S. Jeffrey Rosner, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 315 days.

(21) Appl. No.: 09/990,849

(22) Filed: Nov. 21, 2001

(65) Prior Publication Data

US 2003/0095631 A1 May 22, 2003

(51) Int. Cl.[7] ............................................... G01B 15/02
(52) U.S. Cl. ........................ 378/98.8; 378/62; 382/130
(58) Field of Search ...................... 378/98.8, 62, 98.12, 378/19, 25, 21, 22; 250/370.09; 382/130

(56) References Cited

U.S. PATENT DOCUMENTS

| | | | |
|---|---|---|---|
| 5,388,136 A | | 2/1995 | Halliday et al. |
| 5,844,242 A | * | 12/1998 | Jalink, Jr. et al. ....... 250/370.09 |
| 5,912,942 A | | 6/1999 | Schick et al. |
| 6,055,292 A | * | 4/2000 | Zeller et al. ................... 378/21 |
| 6,078,699 A | * | 6/2000 | Lobregt et al. .............. 382/284 |
| 6,097,833 A | * | 8/2000 | Lobregt et al. .............. 382/130 |
| 6,130,932 A | * | 10/2000 | Diepstraten ................. 378/98.7 |
| 6,215,848 B1 | * | 4/2001 | Linders et al. ............ 378/98.12 |
| 6,483,890 B1 | * | 11/2002 | Malamud ...................... 378/22 |

* cited by examiner

Primary Examiner—David V. Bruce
Assistant Examiner—Irakli Kiknadze

(57) ABSTRACT

An x-ray imaging system includes an x-ray source for projecting imaging radiation onto a sampled object that is secured by a support member and a detector support assembly having multiple detecting modules distributed in a sparse configuration for detecting imaging radiation that has passed through the object. The x-ray source and the detector support assembly are on opposite sides of the support member. Relative displacement is provided between the object and the imaging radiation. By providing the relative displacements and illuminating the object with pulses of imaging radiation at selected intervals, a time series of successive sub-images corresponding to overlapping regions of the object is captured by each module. Computational algorithms combine the captured sub-images to form a composite three-dimensional description of the sampled object. There are multiple pulses of x-ray illumination for each region of the object, and each pulse irradiates more than one detecting module.

22 Claims, 8 Drawing Sheets

SYSTEM FOR COLLECTING MULTIPLE X-RAY IMAGE EXPOSURES OF A SAMPLE USING A SPARSE CONFIGURATION

TECHNICAL FIELD

The invention relates generally to x-ray imaging and more particularly to an x-ray system for producing three-dimensional images.

BACKGROUND ART

Substantial development has been made in the field of x-ray imaging since the discovery of the penetrating capability of x-ray radiation. In many applications, radiography is still utilized to produce a simple two-dimensional projected image, but developments have been made to add modalities to this framework. Although developed in the 1930's, mathematical algorithms for tomography (i.e., the reconstruction of a three-dimensional image of an object from a set of cross-sectional two-dimensional detections) have only recently been exploited, with the evolution of computer-aided tomography (CAT) technology.

In the medical field a CAT system is used for detecting images representing internal parts of a patient's body, such as a heart or stomach, for subsequent diagnosis and treatment. A typical medical CAT system synchronously rotates a radiation source and a corresponding singular large array detector to "scan" a set of radiographs and then compute slices of planar cross-sectional views of the interior of a human body utilizing reconstruction algorithms.

In the electronics part fabrication field, a CAT system may be used during a quality control phase to monitor the state of soldered joints for electrical components, such as printed circuit boards (PCBs). Without requiring physical, visual or electrical access, defects such as shorts, opens, insufficient/excess solder, misaligned and missing components, and reversed polarized capacitors, can be detected. Other products commonly subjected to x-ray inspection include cellular and wireless phones, notebook computers, routers, switches, and PC motherboards. A typical electronic CAT system includes a fixed x-ray source for projecting imaging radiation onto a movable object. A fixed continuous detector array located on a side of the object opposite to the x-ray source captures the sampled radiation that has passed through the object. In a case where the area of the sampled object to be imaged is larger than a field of view of the imaging system, the object and/or the source must be moved in order to obtain multiple views. A disadvantage with this approach is that there is a time delay associated with the repetitive start-and-stop motion, since data relating to the sampled radiation cannot be continuously taken.

In the field of tomography, an important process parameter in collecting data for assembling three-dimensional information is to obtain a wide range of angular projections of the radiation that has passed through the sampled object. The tomographic angle is defined for each arbitrarily small region of the sampled object as the angular range of the projected views that have been collected through this region. For example, two rays through a point inclined oppositely 30 degrees from the normal to the sampled object would create a data set having a tomographic angle of 60 degrees. Accordingly, a large number of two-dimensional views captured by an x-ray detector at different angular projections is required in order to build a sufficient data set. Mathematical algorithms reconstruct the three-dimensional image by computationally combining the two-dimensional views captured at the various angles. This computational combination can be either tomographic or tomosynthetic. In tomographic reconstruction, non-linear reconstruction algorithms converge a hypothetical three-dimensional description to the available data set. In tomosynthetic reconstruction, reasonably simple arithmetic and linear operations calculate a three-dimensional description from the available data set.

One conventional x-ray detection technique utilizes photosensitive film for capturing an image. However, the drawbacks of utilizing film include the use of chemicals for film development and the requirement of a time-consuming development process. Recent advances have eliminated the need of film. In one available system, a scintillator converts x-ray radiation that has propagated through the sampled object of interest into visible light, and a charged coupled device (CCD) converts the light into electrical signals for processing in the digital domain. Other filmless systems employ complementary metal oxide semiconductor (CMOS) pixel sensors.

Notwithstanding the advances made in x-ray detection techniques, an array of sensor elements for capturing a contiguous image is commonly used. Several disadvantages and problems are associated with a continuous array of sensor elements. First, if any detecting element (e.g., one pixel sensor) of the array become defective, replacement of the entire array may be required. Second, if the image captured by the continuous array includes regions of the sampled object not required for diagnosis, the data acquisition rate is unnecessarily extended. Third, since it is critical in collecting images for use in computing three dimensional information to obtain the largest possible tomographic angle in the data set, the requirement of a single contiguous detector can either limit the tomographic angle for a given active area of detector or increase the cost unnecessarily.

Consequently, what is needed is an x-ray imaging system having a detecting arrangement that allows for reliability, efficiency, and manufacturing and operational cost savings.

SUMMARY OF THE INVENTION

The invention is an x-ray imaging system that utilizes multiple detecting modules distributed in a sparse configuration for detecting sub-image data sets with a large tomographic angle of regions of a three-dimensional object. The x-ray imaging system comprises: (1) an x-ray source for projecting pulses of imaging radiation onto a sampled object, (2) a support member on which the sampled object is placed, and (3) a detector assembly having multiple detecting modules sparsely distributed for detecting imaging radiation that has passed through the object. A sparse configuration is herein defined as an arrangement of detecting modules in which each detecting module is spaced apart from an adjacent detecting module by an intermediate distance. In one embodiment, the intermediate distance is greater than the pixel spacing within the module. A projected pulse of radiation is directed at the object from a single addressable point at the x-ray source for a clearly defined period of time. The x-ray source and the detector assembly are on opposite sides of the support member. For each area-wide pulse of radiation that is projected onto the object at various angles, a data sample of sub-images of non-overlapping regions is captured. Moreover, by manipulating the relative position of the object with respect to the imaging radiation projected from the source and by illuminating the object with pulses of radiation at selected intervals, a time series of successive sub-images corresponding to overlapping regions of the object are captured by each detecting module. Variations of existing mathematical algorithms reconstruct the captured sub-images to form a composite tomographic or tomosynthetic image. In one application, the sampled object is a printed circuit board (PCB).

The detector assembly also includes a supporting structure for the placement of the sparsely distributed detecting modules. The modules may be identical, but each module is coupled to a dedicated readout channel for data transmissions that are electrically isolated from each neighboring module. Thus, if a module becomes non-functional, the sparse configuration of modules enables part replacement to be limited to the defective module, rather than the entire detecting array.

In the sparse configuration, each module is strategically located on the supporting structure and is spaced apart by an intermediate distance from a neighboring module. The distance between each neighboring module may be determined on the basis of various factors, such as the specific application, economics (e.g., cost savings), and the desired throughput rate. The distance between modules may be one-quarter of the lateral dimensions of the modules, but is preferably at least as great as this lateral dimension.

Each detecting module includes a two-dimensional array of sensor elements for sensing the intensity of the imaging radiation emerging from a sampled region. In one embodiment, the sensor elements are complementary metal oxide semiconductor (CMOS) pixel sensors coupled to x-ray scintillating materials. Alternatively, the sensor elements are charged coupled devices (CCDs). In yet another embodiment, utilizing a solid-state material that converts x-ray photons directly to electron-hole pairs (e.g., CdTe, CdZnTe) and directly coupling this material to a CMOS readout array eliminates the need to provide a scintillator for converting the radiation to visible light prior to detection.

An x-ray source may include a source tube and optics for projecting pulses of imaging radiation from a continuous region onto the sampled object. The continuous region may be a "spot," which is herein defined as an area on the anode (or illuminating surface) of generally circular shape from which the imaging radiation is projected in a broad range of angles. The projected penetrating radiation causes each sub-image of a region of the sampled object to be captured at a unique projecting angle. The projecting angle is defined as the angle of incidence measured between the normal of the module and the sampled radiation that is projected onto the module.

For each pulse of imaging radiation that is projected, sub images of multiple non-overlapping regions are captured by the modules, with each module receiving imaging radiation from a range of projected angles.

Accordingly, each capture by a respective module may subsequently be used in forming an image of the object.

In accordance with the invention, the x-ray source and the sampled object are configured to achieve relative displacements between the imaging radiation and the sampled object. These displacements may occur during the time between successive pulses. Preferably, manipulation of the x-ray spot provides the primary displacement for the collection of data sets of the targeted region. For example, the source may be physically moved or the spot within the source is moved. The x-ray spot is formed by bringing a high energy finely focused beam of electrons (30 to 250 kV or greater) to strike a target typically fabricated from an efficient x-ray fluorescing material with suitable melting point and stopping power (e.g., Cu, Mo, W). Both by natural fluorescence and brehmstrahlung processes, a broad spectrum of x-ray photons is emitted over a wide range of angles. The position of the spot can arbitrarily be set simply by positioning the beam of electrons within the source—a procedure very similar to the operation of a scanning electron microscope.

The relative displacement between the projected x-ray radiation from the source and the object may be provided by linearly moving the support member in one direction (e.g., x direction) and the x-ray spot position in a perpendicular direction (e.g., y direction). Alternatively, the x-ray source position can be moved. In other embodiments, relative displacements include moving the x-ray spot position or the support member in both the x and y directions. The x-ray spot position and/or the support member can be configured to move in incremental steps or at uniform velocity. The generation of the pulses should be frequent (i.e., more than one pulse generated per object region), so that the time series of sub-images captured by each detecting module is of overlapping regions of the object. An increase in the sparsity of the detecting modules (e.g., the intermediate distances between modules are at least as great as the side-to-side distance across a module) necessitates an increase in the number of pulses per region examined, if a desired result quality for the reconstructed image is to be maintained. That is, there is a tradeoff between reducing manufacturing costs by decreasing the module density for a given-size detector assembly and the throughput enabled rate to maintain a given image rendering.

For each sub-image captured by each detecting module, parameter data must be identified. The parameter data includes position data that is indicative of the position of the "current" pulse relative to the sampled object at the time that the sub-image was captured and includes angular data that indicates the projection angle for the sub-image. Moreover, timing data corresponding to the time interval between pulses during relative displacement at constant velocity may be identified. The sub-images and the corresponding parameter data are transmitted to an integrator unit. Depending on the type of computational algorithm used for reconstruction, different sets of parameter data are used for reconstructing the sub-images into a composite three-dimensional image (sometimes referred to as a "description") of the object or a two-dimensional slice from the three-dimensional image.

One of the advantages of the sparse configuration is that manufacturing costs are reduced as a result of the reduction in the total number of sensor elements, thereby allowing an arbitrary large tomographic angle to be obtained without the scaling costs associated with a large single detector. Additionally, the invention provides the ability to replace a single defective detecting module if it becomes non-functional, rather than replacing the entire detecting array. While the described embodiments are shown as having a number of advantages, other embodiments may not share the same advantages.

DETAILED DESCRIPTION

Figure 1:
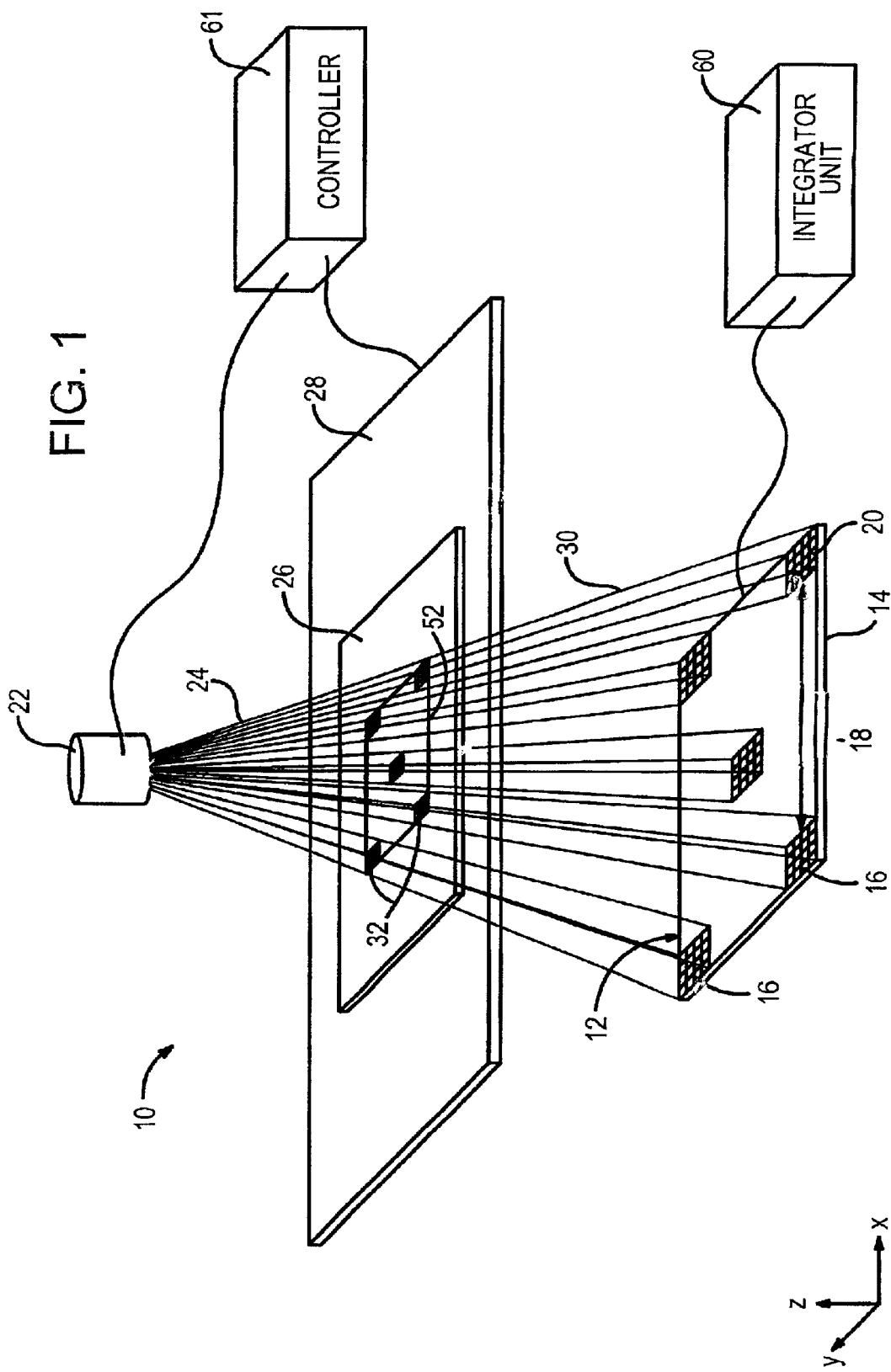
FIG. 1 is a perspective view of an x-ray imaging system, utilizing multiple detecting modules distributed in a sparse configuration in accordance with the invention.

In accordance with the invention, FIG. 1 shows an x-ray imaging is system 10 comprising a detector array 12 having multiple detecting modules distributed in a sparse configuration on a detector support assembly 14. A sparse configuration is herein defined as arrangement of detecting modules in which each detecting module is spaced apart from an adjacent detecting module by an intermediate distance. Hence, non-continuous images of non-continuous regions of the object are captured for each pulse of imaging radiation by the arrangement of detecting modules. Each detecting module 16 is strategically located on the detector support assembly and is spaced apart by an intermediate distance 18 from a neighboring detecting module 20. The area corresponding to the intermediate distance between the detecting module and the neighboring detecting module has no detecting capability.

The x-ray imaging system 10 includes an x-ray source 22 for projecting pulses of penetrating radiation 24 onto a sampled object 26. The sampled object is secured to a support member 28. The support member should be transparent to the penetrating radiation or should have an opening aligned with the sampled object. The detecting module 16 of the array 12 captures emerging "sampled radiation (hereinafter sampled radiation 30") that has passed through the object and intersecting the detecting module. The captured sub-image corresponds to a particular sampled region 32 of the object. In one application, the imaging system 10 allows the detection of board features (e.g., solder joints, electrical traces, multi-chip modules, or stacked chip assemblies) on single-sided and double-sided printed circuit boards (PCBs), even when these features have limited visual and electrical access.

Figure 2:
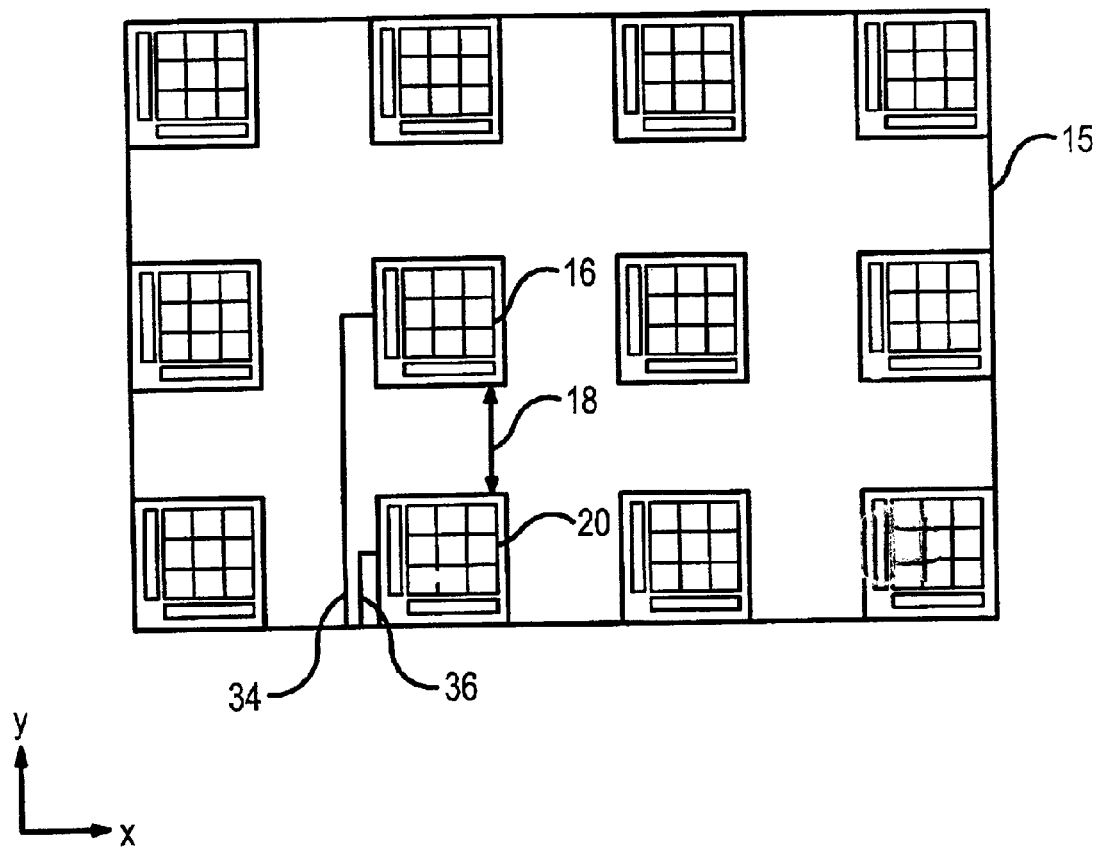
FIG. 2 is a top-view of the detector assembly of the x-ray imaging system of FIG. 1 having multiple modules with respective readout channels.

The detector support assembly 14 is a supporting structure for the placement of multiple sparsely distributed detecting modules, including modules 16 and 20. In one embodiment, the structure is a substrate made of a material such as polymer, glass, silicon, metal or ceramic. In an alternative embodiment, the structure is a PCB having mounting brackets for individual modules and having electrical traces for data transmissions. A dedicated readout channel or a plurality of dedicated readout channels is provided for each module to facilitate electrical isolation between neighboring modules. Thus, a single defective module can be replaced if it becomes non-functional, as opposed to replacing the entire detecting array. Moreover, the dedicated channel(s) facilitates high speed of data readout between radiation pulses. FIG. 2 shows a top-view of an alternate detector support assembly 15 having modules 16 and 20 with dedicated readout channels 34 and 36. While only two dedicated channels 34 and 36 and no power connections are shown, there is an independent channel or a set of readout lines provided for each module. Moreover, the placement of the channels and power connections on top of the assembly 14 is not critical to the invention. Alternatively, the channels can be embedded within the assembly.

Figure 3:
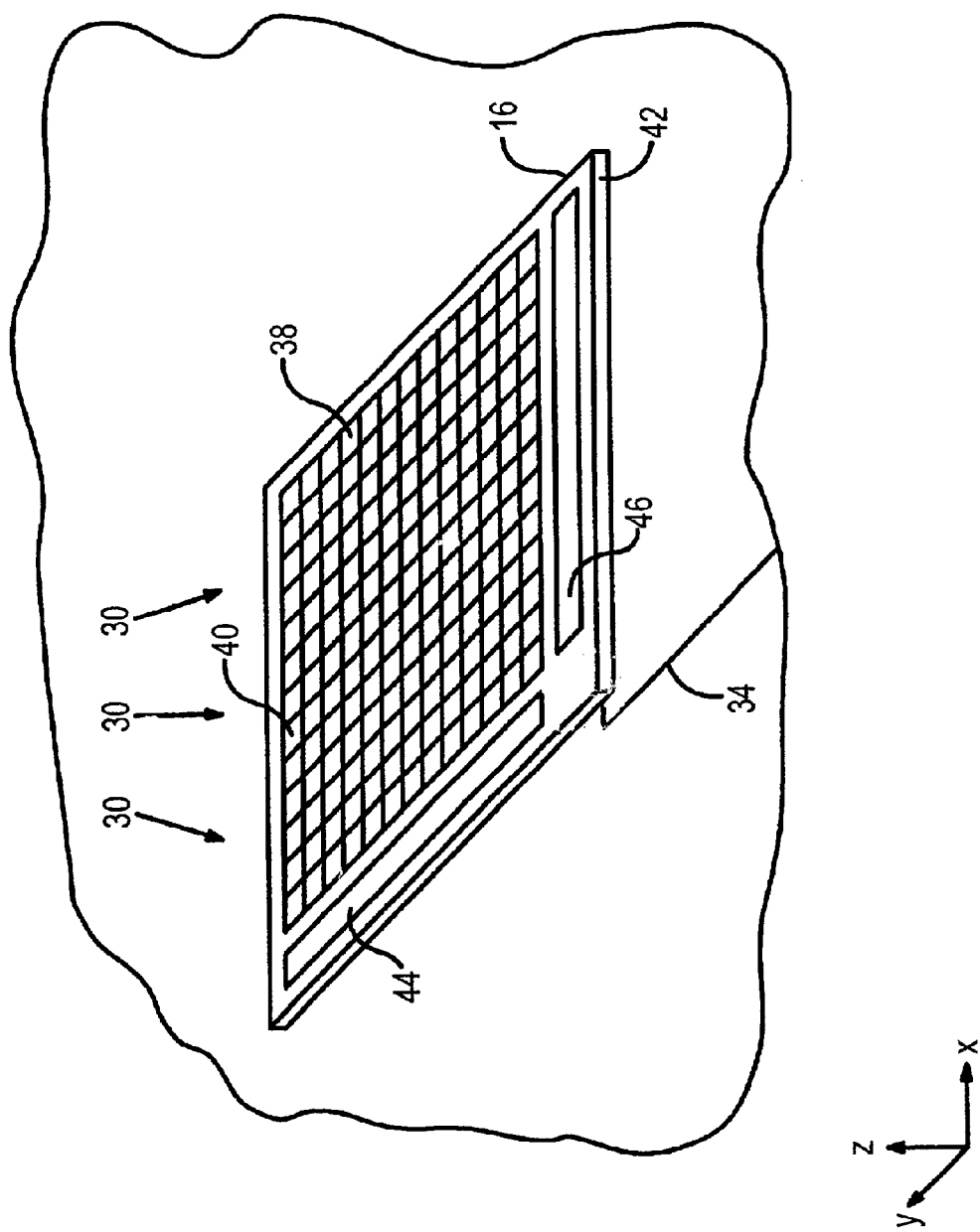
FIG. 3 is a perspective view of a detecting module of FIG. 2 having a two-dimensional array of sensor elements.

Each detecting module of the sparse array 12 includes a two-dimensional array of N×M sensor elements. FIG. 3 is a perspective view of the detecting module 16 with a two-dimensional array 38 of sensor elements 40. All of the other modules have a similar structure. Each sensor element 40 is a radiation sensitive pixel (hereinafter "readout pixel") configured to sense the intensity of the sampled radiation 30. The array is formed or assembled on or within a supporting structure 42 that may be formed from a material similar to the detector support assembly 14. This assembly may be monolithic, as in an integrated circuit or a thin film circuit assembly, or a hybrid assembly where sub-components are manufactured separately and brought together in final assembly with fasteners, adhesives, solders, and the like. A column shift register 44 and a row shift register 46 sequentially read out the sensed signals from each sensor element, using techniques that are well known in the art. The placement of the registers is not critical to the invention. For example, the registers can be embedded within the module. Internal readout circuitry (not shown), such as a multiplexer and a signal driver, transmits the sensed signals via the dedicated readout channel 34 to an integrator unit for processing. While the array 38 is shown as having an identifiable number of sensor elements, other embodiments may include a different number of sensor elements, depending upon various factors, such as the type of application. A module having a fewer number of sensor elements allows a shorter readout time. Depending on the applications, the sensor elements can be complementary metal oxide semiconductor (CMOS), charged coupled devices (CCDS) and the like. While the invention has been described as having modules with a similar structure, this is not critical. One sub-group of modules on the detector array may have a similar type of structure, while another sub-group can have a different type of structure.

Since continuous x-ray imaging radiation is potentially damaging to electrical components and over a period of time can drastically reduce their operational life-spans, a simple scintillator can be replaced with a thick fiber optic plate with a deposited scintillator to protect the sensor elements.

Figure 4:
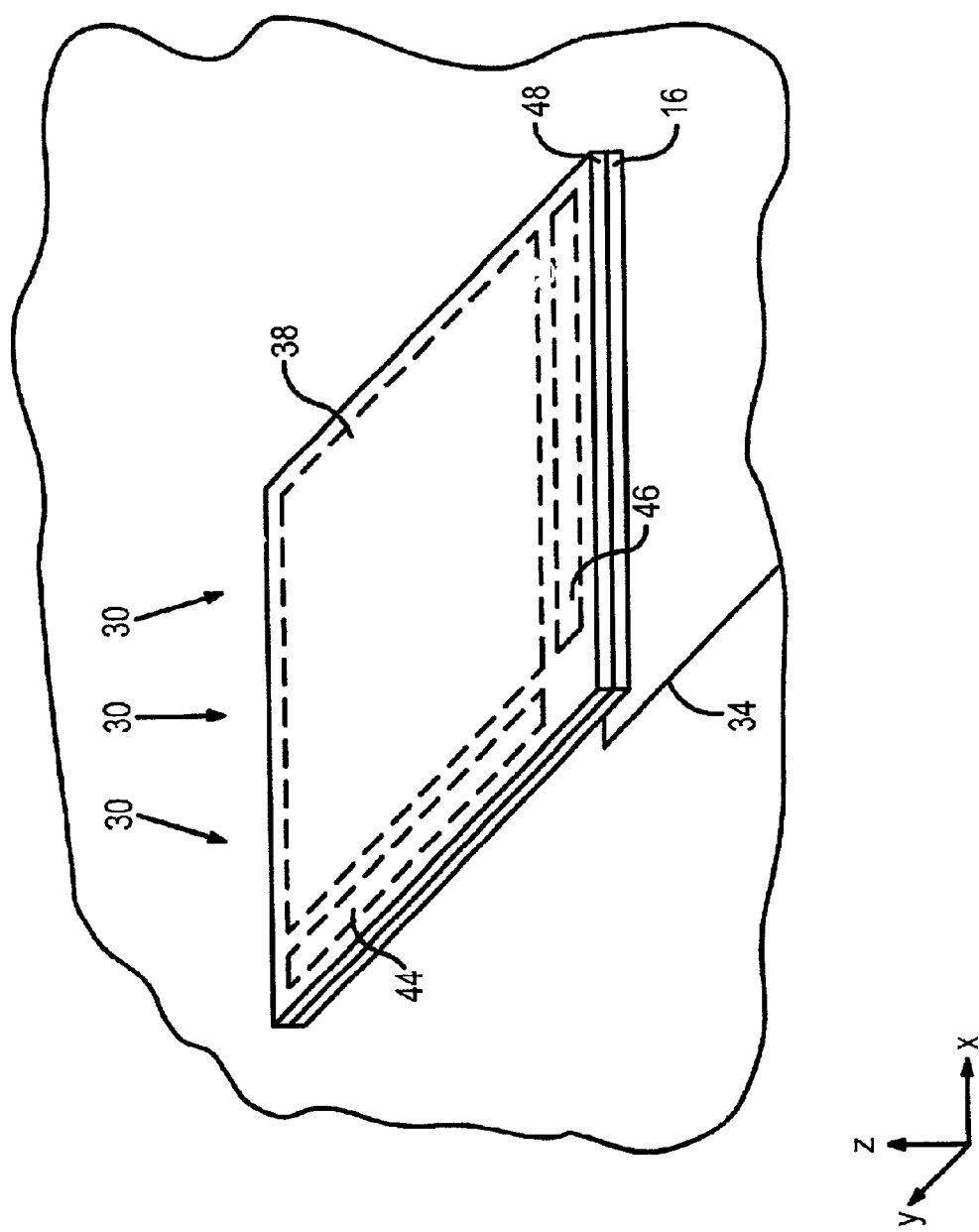
FIG. 4 is a perspective view of the detecting module of FIG. 3 having a radiation-shielding pad.

Ordinary shielding can be used to protect the auxiliary circuitry of the detector modules. FIG. 4 is a perspective view of an exemplary radiation shield 48 placed between the sampled radiation 30 emerging from the sampled object 26 and the detecting module 16. While the array 38 must be available to the radiation, the column shift register 44 and the row shift register 46 are shown as dashed blocks and are shielded from the sampled radiation by the radiation shield. Although this embodiment is shown as utilizing the radiation shield for protecting the sensor elements, other embodiments may not utilize radiation shields. Conversely, a non-scintillating method is also possible, since a sufficiently inexpensive module can be treated as a consumable element to be replaced after sufficient doses of radiation have rendered it inoperable.

Figure 5A:
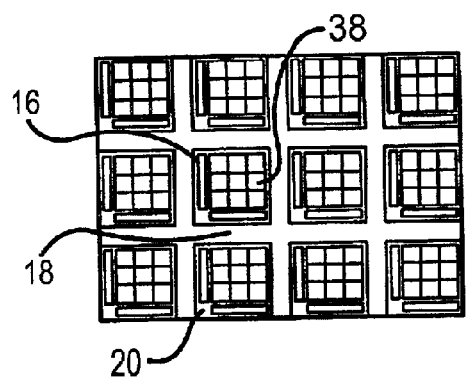
FIG. 5A is a top-view of a sparsely distributed array having multiple modules with each module being spaced apart from a neighboring module by an intermediate distance that is greater than one-quarter of a cross-sectional distance of the two-dimensional array.

Referring back to FIG. 1, the number of detecting modules of the array 12 and the intermediate distance 18 between neighboring modules depend on various factors, such as the type of application, material and manufacturing costs, and the desired throughput rate. Utilizing a greater number of detecting modules will obtain a larger set of projections at a faster rate, as there are more projected views produced for each radiation pulse, thereby generating views with a higher throughput rate, assuming that sufficient computational power can be maintained with the projection generation. On the other hand, utilizing fewer detecting modules reduces the number of electronic components, resulting in savings of manufacturing and operational costs. FIG. 5A shows the detecting module 16 as being spaced apart from a neighboring module 20 by an intermediate distance 18 that is greater than one-quarter of a cross-sectional distance of the two-dimensional array 38.

Figure 5B:
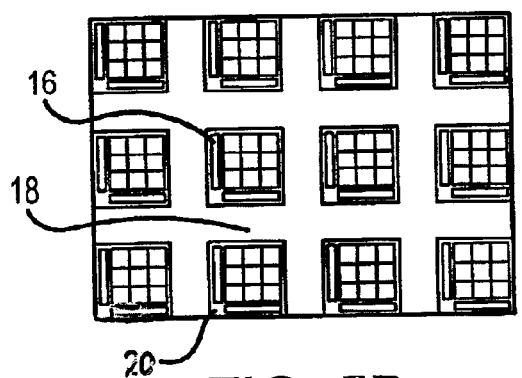
FIG. 5B is a top-view of the array of FIG. 5A where the intermediate distance is greater than one-half of a cross-sectional distance of the two-dimensional array.
Figure 5C:
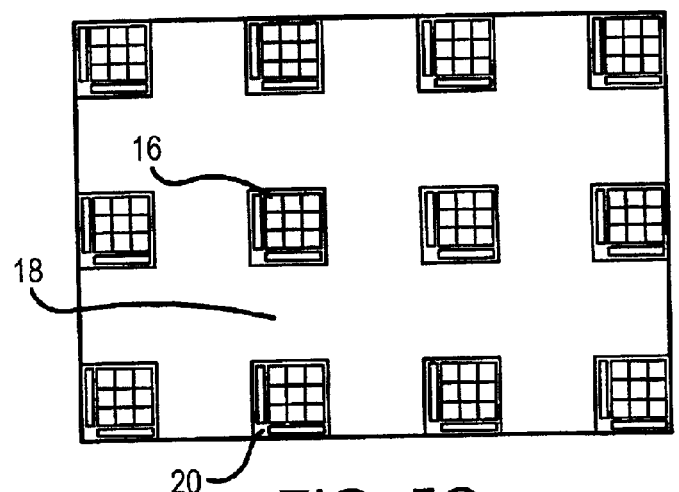
FIG. 5C is a top-view of the array of FIG. 5A where the intermediate distance is at least equal to a cross-sectional distance of the two-dimensional array.

In another embodiment, FIG. 5B shows the distance 18 to be greater than one-half of a cross-sectional distance of the two-dimensional array. In yet another embodiment, FIG. 5C shows the distance to be at least equal to a cross-sectional distance of the two-dimensional array. While FIGS. 5A–5C show a sparse configuration having a checkerboard design, there can be other types of arrangements of sparse configuration, such as circular or elliptical patterns, without diverging from the scope of the invention.

Again returning to FIG. 1, the x-ray source 22 (i.e., the x-ray tube) is provided for illuminating the sampled object 26 with pulses of penetrating radiation 24. The penetrating radiation 24 that is projected onto the detector array 12 defines a corresponding region 52 that includes all the regions on the sampled object that will be imaged by the current radiation pulse. The region 52 is shown as a dashed block to indicate the area of the penetrating radiation that intersects the sampled object. Further, the radiation projecting onto any detector module 16 defines a specific corresponding imaged region 32. If unobstructed by the atomic structures of the object 26 and the support member 28, the radiation leaving the object propagates in a continuous path onto the detector array 12 as the sampled radiation 30. Preferably, the support member is designed using a material having relatively few x-ray radiation scattering or absorbing properties. The only difference between the projected penetrating radiation 24 and the sampled radiation 30 is a decrease in the intensity level of the sampled radiation as some of the photons are blocked or diverted. While the invention is described as having a single x-ray source 22 for illuminating the sampled object 26, there can be multiple x-ray sources for a given sampled object. The number of sources is not critical to the invention.

Figure 6:
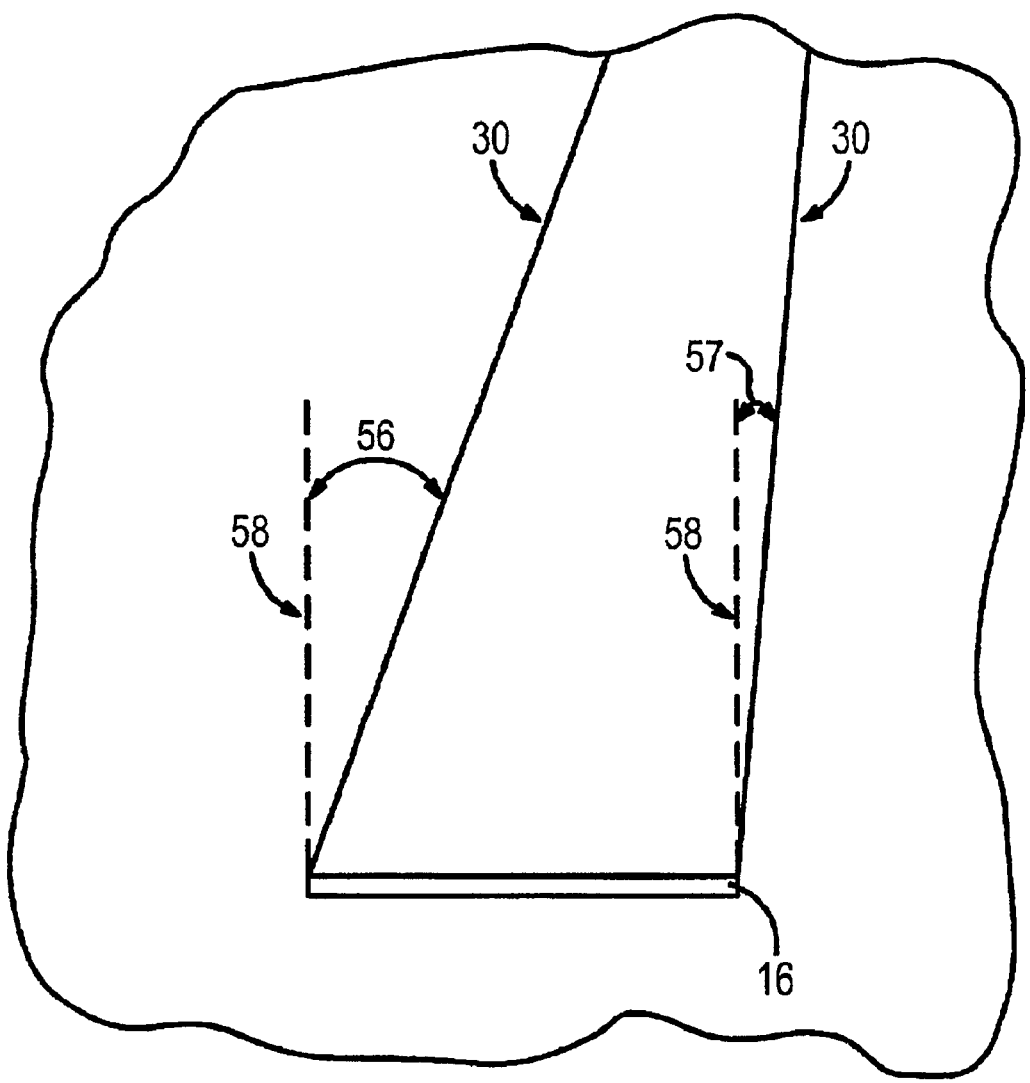
FIG. 6 shows two projection angles formed by a pulse of radiation sampled by a single module.

The penetrating radiation 24 is projected from a spot on the source 22 onto the object 26 in a broad range of angles. The sampled radiation 30 that has passed through the object provides imaging information whenever it intersects an active detector module 16. As shown in FIG. 1, the penetrating and sampled radiation travel in straight lines from the spot to the detector, thereby defining corresponding regions 32 on the object from which the images are formed for the current pulse. Each incident ray of sampled radiation is captured by the detecting modules at a particular projected angle. In one geometry with reference to FIGS. 1 and 6, the exemplary projected angle 56 or 57 is the angle of incidence measured between the normal 58 of the detecting module 16 and the sampled radiations 30 that are projected onto the module. While projected angles 56 and 57 define the extrema of projection angles intercepted by the module, there are additional projection angles (not shown) between the two extrema. Signals corresponding to the captured sampled radiation 30, along with its associated projected angle, detected by each sensing element 40 of the module 16 are transmitted to an integrator unit 60 for processing (i.e., computational combining). In the embodiment in which there are multiple modules 16 and 20, multiple incident rays of sampled radiation are captured at various projected angles. Consequently, a range of projection angles is captured and can be subsequently used to reconstruct a three-dimensional image or a two-dimensional slice.

A controller 61 of the imaging system 10 of FIG. 1 is configured to regulate relative movement between the penetrating radiation 24 and the sampled object 26. The controller is coupled to the support member 28 and the x-ray source 22. Preferably, the support member 28 on which the sampled object is placed is configured to move along the x axis. Linear movement of the support member results in a corresponding linear displacement of the sampled object. Consequently, linear movement coupled with the illumination of an x-ray pulse allow sub-images of different regions along a linear path of the object to be captured by corresponding detecting modules. Also in the preferred embodiment, manipulation of the x-ray spot provides the primary displacement along the y axis for the collection of data sets of the different regions. For example, the source may be physically moved or the x-ray spot may be electronically moved. Coupled with x-ray illumination, linear movements along the y axis allow the capture of sub-images of different regions in a path perpendicular to that of the support member 28. Combining linear movements along the x and y axes allows an effective sampling of the object 26 in a diagonal path. In an alternative embodiment, the support member 28 is configured to move in both the x and y directions, while the projection of the x-ray radiation from the source 22 remains stationary. In yet another alternative embodiment, the projection of the radiation is configured to move in both the x and y directions, while the support member remains stationary.

Relative movement along the x and y directions can either be at a constant velocity or in incremental steps. In the preferred embodiment, relative movement is at the constant velocity, so that the support member 28 and/or the projection of the radiation from the x-ray source 22 are continuously displaced during operation, i.e., without starting and stopping as pulses of x-ray radiation are generated at selected intervals. The time intervals between the pulses are accurately controlled. Signals corresponding to each sub-image are read by the detecting module 16 between successive x-ray illuminations. Knowledge of the time intervals between the pulses and the direction of the relative movement allows a determination of the relative displacement and the exact location of the object. The time intervals between the pulses during relative movement at uniform velocity must be selected to give a sufficient data set of projected angles corresponding to the captured sub-images in order to generate an adequate computed description of the sampled object. Moreover, the strobe time of the x-ray source 22 (i.e., the period the source is illuminating) is chosen to be abrupt enough to appropriately minimize blurring during movement. An effective shutter or electron beam-blanking apparatus having a rapid exposure time can be used.

For relative movement in incremental steps, the support member 28 and/or the projection of the radiation from the source 22 are repetitively displaced and stopped during operation according to a pre-determined grid of source points. Each time the support member is stopped, a pulse of x-ray radiation is generated. Sub-images corresponding to different regions, including region 32, of the sampled object are detected by the detecting modules. Signals corresponding to each sub-image are read by the detecting module prior to a subsequent incremental step.

A primary advantage of relative movement at uniform velocity is the elimination of "motion dead time." That is, the time required for movement to reach the target velocity and to stop movement, when no x-ray illumination can be projected and no data can be taken, is eliminated. Consequently, data corresponding to the sampled radiation 30 can be generated and read from each module during constant velocity at a faster rate.

As stated earlier, illuminating the sampled object 26 with a pulse of x-ray radiation permits the sampling of particular regions (e.g., region 32) of the object by the detecting modules. In the preferred embodiment, in which the frequency of the pulses from the x-ray source 22 is significantly greater than one pulse of radiation for every discrete object region, successive sub-images corresponding to overlapping portions of a particular object region are captured.

Figure 7C:
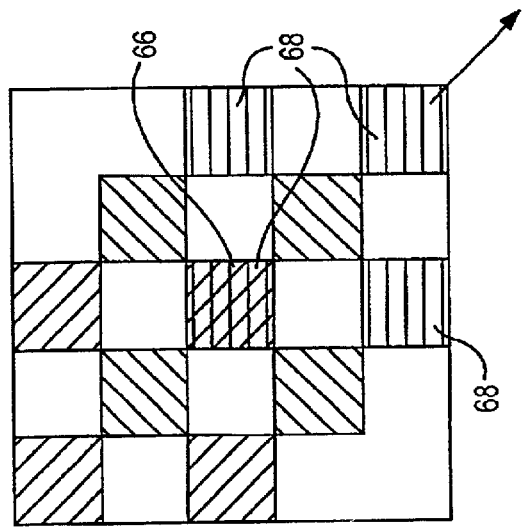
FIGS. 7A through 7C provide a successive series of sub-images corresponding to adjoining regions as pulses of radiation are generated during relative displacement.
Figure 7B:
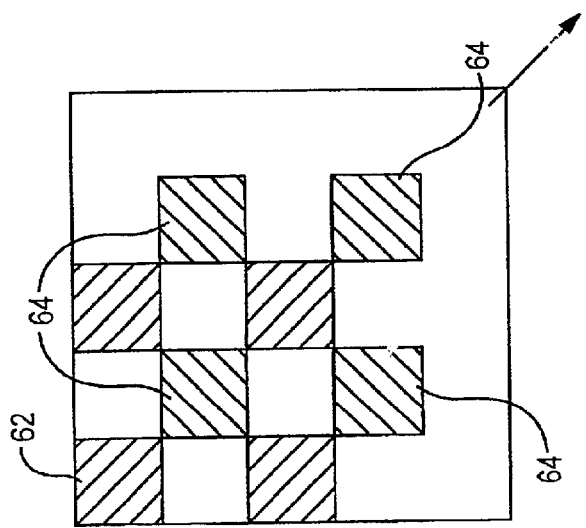
Figure 7A:
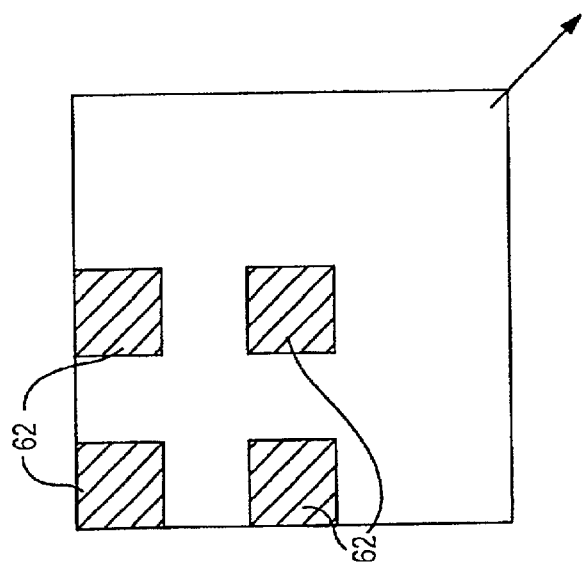

Referring to FIGS. 7A–7C, a series of successive sub-images is captured by the detecting modules 16 for corresponding regions 32 of the sampled object 26 of FIG. 1 as pulses of radiation are generated during the relative displacement between the sampled object and the radiation. In the figures, the relative displacement is in a diagonal direction in relation to the modules, as indicated by the direction of the arrows. FIG. 7A shows the locations on the object of captured first sub-images 62. Each sub-image 62 corresponds to a different sampled region 32 of the object 26. The shape of each sub-image is scaled to the shape of detector modules in the detector array. Along with the capture of each sub-image, parameter data (including the projection angles of the incident sampling radiation) is identified.

FIG. 7B shows the locations of captured second sub-images 64 with the superimposed locations of the captured first sub-images 62 after relative displacement in the diagonal direction. FIGS. 7A and 7B do not contain any image information of any common region, but rather, collectively, double the area of the object from which image information has been obtained.

FIG. 7C adds the locations of captured third sub-images 68 after further relative displacement and includes both added information about new regions and new information with a distinctly different set of projection angles to a common region 66, as indicated by the superimposed cross-hatching. Therefore, the common region is imaged by data of a captured first sub-image 62 and a captured third sub-image 68. The common region represents two sub-images. Algorithms which recognize common images in successive sub-images utilize data associated with the identified projection angles for each sub-image to form a computed description of the PCB or other object.

While the captured sub-images 62, 64 and 68 described in the exemplary embodiment of respective FIGS. 7A, 7B and 7C have only one common area 66, the preferred embodiment captures a large number of intermediate sub-images and identified projection angles in order to generate a high resolution tomographic image.

Moreover, although the embodiments of FIGS. 7A–7C include capturing a common area 66 by different detecting modules at different tomographic angles to form a composite three-dimensional image of the region, the same image may be formed from a set of sub-images derived from different pulses of radiation from different detection modules. In such an embodiment, a sub-image captured by a first detection module may be combined with a different sub-image captured by a neighboring second detection module.

Moreover, while the described invention utilizes only one set of detecting modules distributed in a sparse configuration, an alternative embodiment can include more than one set of sparsely distributed modules. In this configuration, two sets of modules can be positioned and alternately illuminated such that one set of modules transmits signals corresponding to the detected sampled radiation 30, while the second set of modules detects the original radiation 24 level, which is used as a reference.

The integrator unit 60 of FIG. 1 includes processing circuitry (not shown) for computationally combining the series of successive sub-images together to form a composite three-dimensional description or a two-dimensional slice of the three-dimensional image. Parameter data such as: (1) angular data identifying projected angles, (2) positional data of the x-ray source, and (3) positional data of the sampled object can be used for computationally combining the successive sub-images for the reconstruction of a composite description of the object, depending on the types of algorithms and data used. The identified parameter data is stated for exemplary purposes and is not meant to be limiting.

Figure 8:
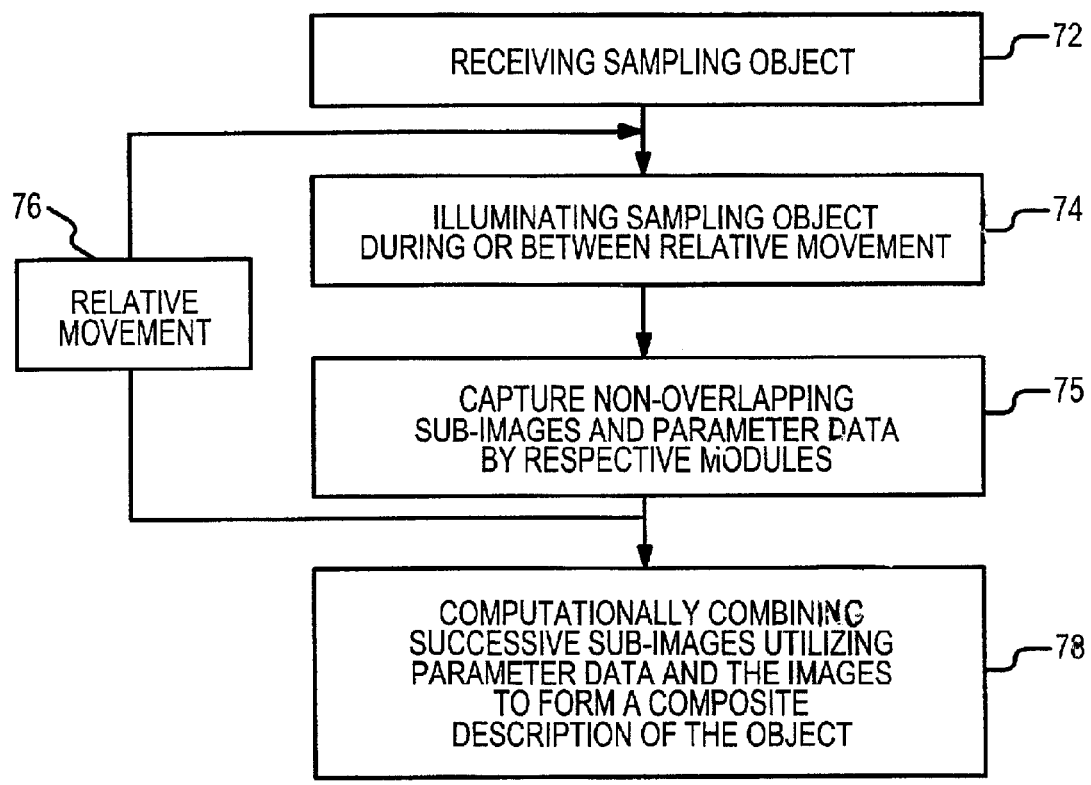
FIG. 8 is a process flow diagram for forming a composite tomographic image in accordance with the invention.

Operation of the imaging system 10 utilizing the sparse configuration of FIG. 1 is described with reference to FIG. 8. A process flow diagram for computationally combining successive sub-images to form a composite three-dimensional image or a two-dimensional slice of the three-dimensional image of the object is identified. In step 72, the sampled object 26 is received by the support member 28 for imaging. In step 74, the sampled object is illuminated with a pulse of x-ray radiation during or between relative displacement between the projection of x-ray radiation from the x-ray source 22 to spot within the source and the sampled object. In step 75, multiple non-overlapping regions of the object along with parameter data associated with each region are captured for each pulse by the modules. In step 76, relative movement is provided and steps 74 and 75 are repeated. The routine allows successive sub-images of features in overlapping regions of the object to be captured by each detecting module, along with parameter data associated with each capture. In step 78, successive sub-images are computationally combined together utilizing parameter data and the sub-images to form a composite description of the sampled object. The step 78 may include algebraic addition of multiple sub-images of the same region of interest after scaling, resampling to change magnification, spatially offsetting to match regions exactly, or adjusting the values to reflect quantitatively the absorption of radiation by the object. Additionally, the computational step may include back projection (filtered or unfiltered) or other tomographic reduction techniques and selecting particular sub-images that are advantageous such that minimum artifacts from shadowing, geometric superposition, and the like, are considered.

As is apparent to those skilled in the art, other modifications are possible without diverging from the scope of the invention. Accordingly, the invention is to be construed in accordance with the following claims.

What is claimed is:

1. An imaging system for imaging a sample of interest comprising:

an emitter enabled to project imaging radiation through said sample of interest, at least one of said emitter and said sample of interest being manipulable such that relative movement between said imaging radiation and said sample of interest is enabled;

a plurality of detecting modules disposed in a sparsely distributed configuration, including a first detecting module that is spaced apart from a neighboring second detecting module, said first and second detecting modules each having an array of sensors that are responsive to said imaging radiation, said detecting modules being cooperatively aligned with said emitter such that multiple said detecting modules are simultaneously irradiated by a continuous pattern of said imaging radiation, said detecting modules being cooperative with said emitter and said sample of interest for detecting regions of said sample of interest to generate series of sub-images during said relative movement between said imaging radiation and said sample of interest, said detecting modules being controlled such that each said detecting module provides a succession of sub-images in which at least some of said sub-images in said succession overlap with respect to imaging common portions of said sample of interest; and an integrating unit coupled to said detecting modules for computationally combining said sub-images on a basis of data that includes (a) angular data indicative of projection angles of said imaging radiation during said imaging of said common portions of said sample of interest and (b) positional data indicative of relative positions of said imaging radiation and said sample of interest in acquiring individual said sub-images.

2. The imaging system of claim 1 wherein said first detecting module and said neighboring second detecting module are coupled to said integrating unit by respective first and second channels, said first channel being independent from said second channel, said integrating unit including processing circuitry for integrating said sub-images to form a composite image of said sample of interest.

3. The imaging system of claim 2 wherein said integrating unit is enabled to generate a three-dimensional image of said sample of interest.

4. The imaging system of claim 1 wherein said detecting modules each include a substrate having a physically discrete array of sensors, said substrates being individually connected to a supporting structure.

5. The imaging system of claim 1 wherein said emitter is an x-ray tube for projecting x-ray radiation, said emitter and said detecting module being on opposite sides of said sample of interest.

6. An x-ray imager for generating an image of an object comprising:
   an x-ray source for projecting a pulse of x-ray radiation through said object, said pulse being projected from a continuous region of said source; and
   a plurality of discrete sensor arrays, each said sensor array including a substrate having a two-dimensional pattern of sensor elements, at least some of said sensor arrays being spaced apart from adjacent sensor arrays by a distance greater than one-quarter of a cross-sectional distance of said two-dimensional pattern while being sufficiently close to enable said pulse to simultaneously irradiate a plurality of said sensor arrays, said sensor arrays bang arranged for detecting time series of sub-images of overlapping portions of said object, said sub-images in each said time series being distinguishable as a result of relative displacement of said object with respect to said x-ray radiation from said source.

7. The x-ray imager of claim 6 wherein said distance is greater than one-half of said cross-sectional distance of said two-dimensional pattern, said sensor arrays being substantially identical.

8. The x-ay imager of claim 6 wherein said distance is at least equal to said cross sectional distance of said two-dimensional pattern, said sensor arrays being substantially identical.

9. The x-ray imager of claim 6, wherein said substrate is mounted on a detector support assembly, said detector support assembly including a supporting substrate on which said sensor arrays are individually mounted.

10. The x-ray imager of claim 6 further comprising a controller for sequencing said relative displacement to generate said time series of sub-images and an integrator for computationally combining said sub-images to form one of a three-dimensional image and a two-dimensional slice of said object.

11. The x-ray imager of claim 6 further comprising an assembly for providing said relative displacement such that manipulation of said object is in a first direction and manipulation of said x-ray radiation from said source is in a second direction, said first direction being substantially perpendicular to said second direction.

12. The x-ray imager of claim 6 further comprising an assembly for providing said relative displacement at uniform velocity.

13. The x-ray imager of claim 6 wherein said object is a printed circuit board (PCB).

14. A method of forming a composite image comprising the steps of:
   projecting timed pulses of x-ray radiation from a common source through a sample of interest;
   providing relative movement between projections of said x-ray radiation from said source and said sample of interest;
   exposing a sparsely distributed configuration of area detectors to said pulses after passage through said sample of interest, such that spaced apart regions of said sample of interest are imaged for each of said pulses;
   acquiring a plurality of sub-images corresponding to portions of said sample of interest during said relative movement by said area detector, including associating individual said sub-images with axial direction information indicative of a projection angle of said x-ray radiation in acquiring said individual sub-images and including associating individual said sub-images with position information indicative of relative locations of said source in acquiring said individual sub-images; and
   processing said sub-images to form an image of said sample of interest, including utilizing said axial direction information and said position information in determining formation of said image.

15. The method of claim 14 wherein said stop of acquiring includes collecting a sequence of sub-images corresponding to overlapping regions of said sample of interest by at least one of said area detectors during said relative movement, said stop of processing including integrating said sequence of sub-images to generate said image.

16. The method of claim 15 wherein said step of collecting includes projecting at least one pulse of said x-ray radiation onto said sample for each of said overlapping regions.

17. The method of claim 15 wherein said step of integrating includes computationally combining said sequence of sub-images after at least one of:
   a. scaling,
   b. resampling to change magnification,
   c. offsetting spatially to match regions, and
   d. adjusting to reflect an absorption of said radiation by said sample of interest.

18. The method of claim 17 wherein said step of combining includes algebraically adding said sub-images of said sequence.

19. The method of claim 17 wherein said step of combining includes one of unfiltered backprojecting and filtered backprojecting.

20. The method of claim 17 wherein said step of combining includes selecting said sub-images having minimum artifacts.

21. The method of claim 14 wherein said step of processing said sub-images includes forming a three-dimensional image of said sample of interest.

22. The method of claim 14 wherein said step of exposing said plurality of area detectors includes providing dedicated electrical connection between each of said area detectors and common processing circuitry so as to enable electrical isolation among said area detectors.

* * * * *